United States Patent [19]

Linden

[11] Patent Number: 4,641,076

[45] Date of Patent: Feb. 3, 1987

[54] METHOD AND APPARATUS FOR STERILIZING AND CHARGING BATTERIES

[75] Inventor: Harry A. Linden, Santa Barbara, Calif.

[73] Assignee: Hall Surgical-Division of Zimmer, Inc., Carpinteria, Calif.

[21] Appl. No.: 693,881

[22] Filed: Jan. 23, 1985

[51] Int. Cl.⁴ .............................................. H02J 7/00
[52] U.S. Cl. .................................. 320/2; 128/419 PS
[58] Field of Search ...................... 320/2; 128/419 PS; 422/6, 25

[56] References Cited

U.S. PATENT DOCUMENTS 3,939,391  2/1976  Winnacker ............................... 320/2
4,141,367  2/1979  Ferreira ......................... 128/419 PT
4,288,733  9/1981  Bilanceri et al. .......................... 320/2

*Primary Examiner*—Peter S. Wong
*Assistant Examiner*—Mark D. Simpson
*Attorney, Agent, or Firm*—Stuart E. Kreiger

[57] ABSTRACT

A method and apparatus for providing sterile, charged batteries for use in a sterile field. The method includes the steps of placing at least one battery in a sterilization container, sterilizing the battery within the container, charging the battery while maintaining it in a sterile state within the container, and transferring the sterile, charged battery in a sterile state to the sterile field. The container is adapted to permit the entrance of a sterilant and to prevent the entrance of contaminants. The container may include an integral battery charger adapted to withstand exposure to the environment of a sterilization process. Alternatively, the container may include a connector for releasably electrically connecting the battery housed within the container to a distinct, external battery charger.

10 Claims, 2 Drawing Figures

METHOD AND APPARATUS FOR STERILIZING AND CHARGING BATTERIES

BACKGROUND OF THE INVENTION

1. Field of the Invention

The present invention relates to methods and apparatus of providing sterile, charged batteries, and, more particularly, to a method of and apparatus for charging such batteries following sterilization.

2. Description of the Prior Art

A problem associated with the use of battery powered surgical instruments is the difficulty in providing fully charged sterile batteries. The batteries used to power the instruments must be sterilized prior to introduction into the sterile field. If the batteries are charged before being sterilized, they lose about twenty percent of the charge during the sterilization process. If the batteries are charged after being sterilized, the sterility is compromised by exposure to the battery charger. Manufacturers have not heretofore provided sterile chargers because exposing the chargers to the sterilization process damages them. Some manufacturers have offered a disposable drape that can be placed over the charger. The drape includes terminals so that power can be transferred through it.

The aerospace industry has developed a means of sealing the circuits of motors from exposure to the vacuums in which the motor must operate. The motors do not function in a vacuum. Motors used in undersea work have also been sealed to protect them from the detrimental effects of pressure and salt water.

It is an object of the present invention to provide fully charged batteries for use in a sterile field without the risk of contaminating the batteries after they have been sterilized. It is a further object of the present invention to provide an apparatus for storing and charging the sterile batteries following sterilization without the risk of contamination.

SUMMARY OF THE INVENTION

The present invention provides a method of and apparatus for providing sterile, charged batteries for use in a sterile field. The method includes the steps of placing at least one battery in a sterilization container, sterilizing the battery within the container, charging the battery to a desired voltage while maintaining the battery in a sterile state within the container, and transferring the sterile charged battery in a sterile state to the sterile field. The container is permeable to sterilant but impermeable to contaminants. The container is adapted to provide electrical communication between a battery charger and the battery.

An apparatus for practicing the method of the present invention includes a container adapted to permit the entrance of a sterilant and to prevent the entrance of contaminants. The container is adapted to house at least one battery, and preferably a plurality of batteries, during sterilization and storage. The container includes means for charging the battery within the container while maintaining the battery in a sterile state.

The charging means may be a connector for releasably electrically connecting the battery housed within the container to a battery charger distinct from and external to the container. Alternatively, the container may include an integral battery charger which is sealed to withstand exposure to the environment present during a sterilization process. The integral battery charger may be of the variety described in the co-pending United States Patent Application of John H. Pascaloff entitled METHOD AND APPARATUS FOR PROVIDING STERILE CHARGED BATTERIES which was filed together herewith and is hereby incorporated by reference.

BRIEF DESCRIPTION OF THE DRAWINGS

The following detailed description of the preferred embodiment can better be understood if reference is made to the drawings in which.

DETAILED DESCRIPTION OF THE PREFERRED EMBODIMENTS

Figure 1:
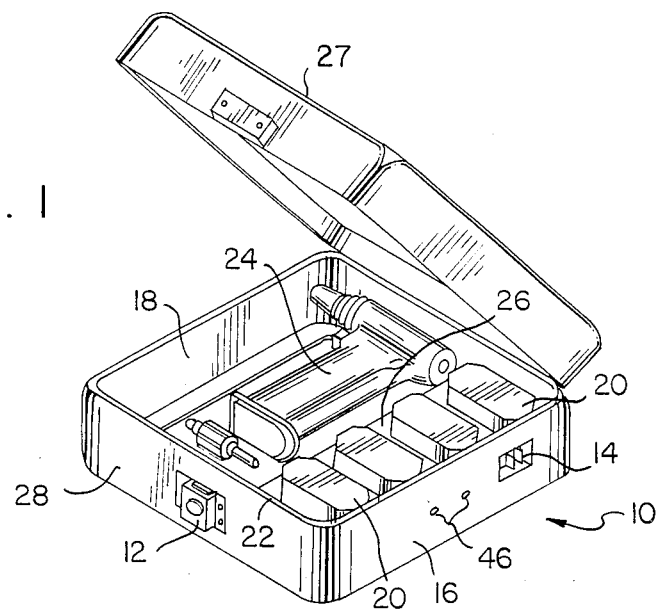
FIG. 1 is a perspective view of the preferred embodiment of the container which may be used to practice the method of the present invention.
Figure 2:
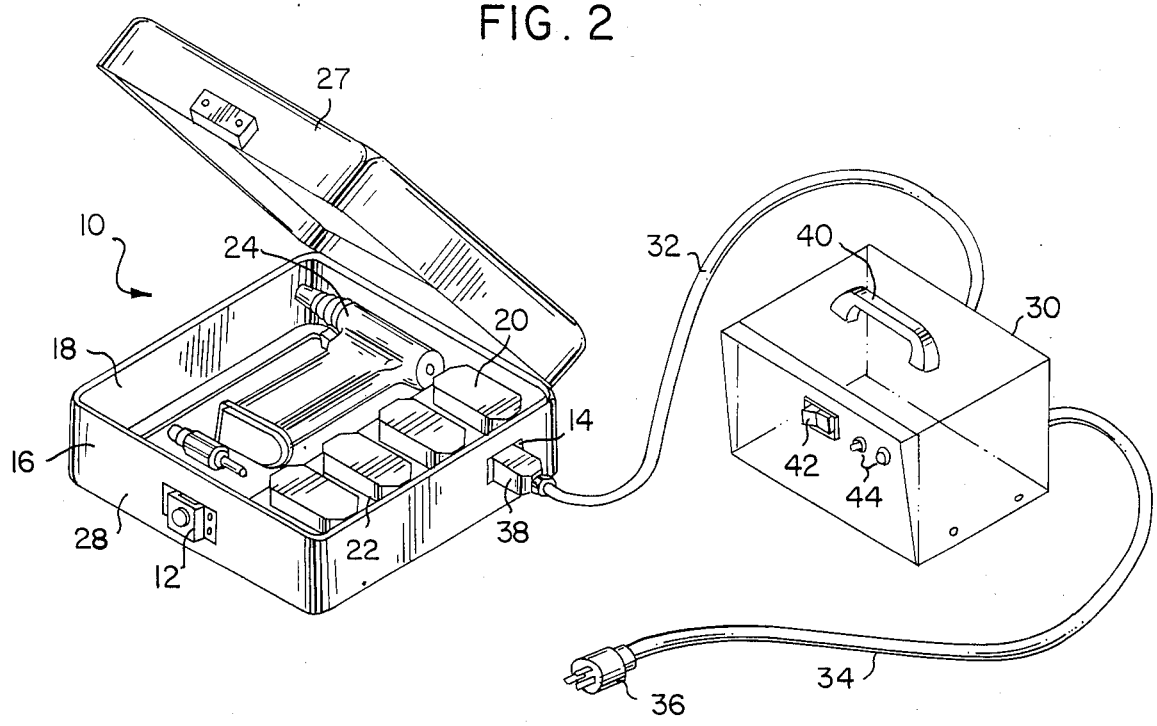
FIG. 2 is a perspective view of the container connected to an external battery charger.

FIGS. 1 and 2 illustrate the preferred embodiments of a container 10 which may be used to practice the method of the present invention.

Container 10 may be any suitable known sterilization container which permits the entry of sterilant but prevents the entry of contaminants when the container is closed so that the sterility of the contents can be maintained in a nonsterile field. Container 10 must also include means to charge batteries 20 within the container. Commercially available sterilization containers, such as the container marketed by the American Sterilizer Company under the trademark EAGLE STERISET, can be appropriately modified to include such a charging means. Other known sterilization containers may be similarly modified to provide the container 10 of the present invention.

Referring to FIG. 1, container 10 includes a bottom portion 28 and a lid 27 which define the interior 18 of container 10. Battery receptacles 22 are provided within container 10 to hold batteries 20 during sterilization, storage and charging. The receptacles 22 include contacts for electrically connecting the batteries 20 to a battery charger, 26 or 30, each of which will be described below. Four batteries 20 are shown, but any number of batteries may be housed in an appropriately sized container 10.

The exterior 16 of container 10 includes a lock 12 to prevent tampering during storage and a connector 14 for releasably electrically connecting container 10 to either an external power source (not shown) or a distinct, external battery charger 30.

Container 10 may be sized to house a battery powdered surgical tool 24 during sterilization and storage in addition to the batteries 20 needed to power the tool 24. The batteries 20 should be of the variety required by the particular tool 24. Sterilizable batteries and sterilizable battery powered surgical tools are commercially available. An assembly of appropriately sized component parts may be provided by the present invention which includes the container 10, batteries 20 and means to charge the batteries 20. The assembly may also include the surgical tool 24.

The means to charge batteries 20 may be an integral battery charger 26 or a distinct, external battery charger 30. The integral battery charger 26 is preferably housed in container 10 adjacent to battery receptacles 22. The integral battery charger 26 is of the variety described in the co-pending United States Patent Application of John H. Pascaloff entitled METHOD AND APPARATUS FOR PROVIDING STERILE CHARGED BATTERIES, referenced above. The charger 26 is adapted to withstand exposure to the environment present during a sterilization process of choice. The electrical components of charger 26 are hermetically sealed and made of materials that will withstand the temperature and pressure extremes present during some sterilization processes or the chemical environment present during others.

In the embodiment of container 10 which includes the integral battery charger 26, connector 14 is connected by any suitable known means to an external power source. Lights 46 on the exterior 16 of container 10 indicate when charging or testing occurs. For example, approximately 115 volts AC may be delivered from a power source through connector 14 to the charger 26. A transformer converts the 115 volts AC to a suitable DC voltage. The charging voltage is delivered to a printed circuit board and the appropriate voltage is delivered to each of the batteries 20. When resting in receptacles 22, batteries 20 are electrically connected to the charger 26.

In this embodiment, the container 10, batteries 20, battery charger 26 and tool 24 are sterilized together. The locked container 10 can then be stored while the tool 24, batteries 20 and battery charger 26 are maintained in a sterile state within container 10. The batteries 20 may be charged while in the container 10 by connecting container 10 by means of external connector 14 to a power source. The charging step may take place in a sterile or a nonsterile location. The interior 18 of container 10 remains in a sterile state throughout the charging step.

In the embodiment of container 10 shown in FIG. 2, connector 14 is electrically connected to a distinct, external battery charger 30. The container 10 does not include an integral battery charger 26 in the embodiment of FIG. 2.

Battery charger 30 may be any known battery charger and need not be sterilizable. Battery charger 30 includes handle 40, switch 42 and display lights 44 to indicate the status of the charging cycle. A line 32 with plug 38 connects the charger 30 to connector 14 and batteries 20 resting in receptacles 22. A line 34 with plug 36 connects the charger 30 to a power source. Charger 30 can be used to supply charge to several containers 10 following sterilization of batteries 20.

The method of the present invention may be practiced with container 10 by placing at least one battery 20 in a receptacle 22 of container 10 and sterilizing the battery or batteries 20 within container 10 by a desired sterilization process. Sterilization processes include steam, ethylene oxide or hydrogen peroxide, or glutaraldehyde. Following completion of the sterilizing step, the container 10 with the now sterilized batteries 20 may be stored until needed for use. Following sterilization, during storage or any time before use, the batteries 20 are charged to a desired voltage while maintained in a sterile state within the container 10. The sterile, charged batteries are then transferred in a sterile state to a sterile field. The tool 24 may also be sterilized and stored in container 10.

The transfer may occur by having a nonsterile person carry container 10 to the sterile field. The nonsterile person opens the container 10 and a sterile person removes batteries 20 from the container.

In the embodiment of container 10 shown in FIG. 2 the charging step is achieved by electrically connecting container 10 to the external battery charger 30. Plug 38 is inserted into connector 14 and plug 36 is connected to a suitable power source. Switch 42 is turned on to activate charger 30. Charge is transferred from the power soure, through battery charger 30, connector 14 and receptacle contacts to batteries 20 without exposing batteries 20 to the nonsterile environment outside of container 10.

In the embodiment of container 10 shown in FIG. 1, a suitable cord connects connector 14 to a power source. The integral charger 26 receives the charge through the connector 14 and transfers the desired charging voltage to batteries 20 in receptacles 22. In this manner, the batteries 20 can be fully charged following sterilization without risking contamination of the batteries 20. Charging using the integral charger 26 may occur in a nonsterile or a sterile field. As long as the cord connecting connector 14 to the power source is sterile or is connected in a manner which avoids contact with a surface in the sterile field, the sterility of the sterile field will be maintained.

The apparatus and method of the present invention provides sterile, fully charged batteries for use in a sterile field. By sterilizing, storing and charging the batteries 20, within container 10 and transferring the fully charged, sterile batteries to the sterile field in container 10, the problems of lost charge during sterilization and nonsterile storage or transfer techniques are avoided.

What is claimed is:

1. A method of providing sterile, charged batteries for use in a sterile field comprising the steps of:
   placing at least one battery in a sterilization container;
   sterilizing said battery within said container;
   charging said battery to a desired voltage while maintaining said battery in a sterile state within said container; and
   transferring said sterile, charged battery in a sterile state to the sterile field, said container being permeable to sterilant but impermeable to contaminants and being adapted to provide electrical communication between a battery charger and said battery.

2. A method as recited in claim 1 wherein said battery is charged by electrically connecting said container to an external battery charger.

3. Apparatus for providing at least one sterile, charged battery for use in a sterile field comprising:
   a container adapted to permit the entrance of a sterilant and to prevent the entrance of contaminants, said container being adapted to house said battery during sterilization and storage, and said container having means for charging said battery therein while maintaining said battery in a sterile state.

4. Apparatus as recited in claim 3 wherein said charging means is a battery charger integrally connected to said container and adapted to withstand exposure to the environment during sterilization.

5. Apparatus as recited in claim 4 wherein said battery charger is hermetically sealed.

6. Apparatus as recited in claim 3 wherein said charging means is a connector for releasably electrically connecting said battery housed within said container to a battery charger distinct from and external to said container.

7. An assembly for providing sterile, charged batteries for use in a sterile field comprising:

a container, at least one battery and a battery charger;

said container being adapted to permit the entrance of a sterilant and to prevent the entrance of contaminants and said container being adapted to so house said at least one battery that said battery is sterilized within said container when said container is exposed to a sterilization process and said battery is maintained in a sterile state when stored in said container subsequent to the exposure to said sterilization process; and said container having means to electrically connect said battery to said battery charger for charging said battery within said container while maintaining said battery in said sterile state.

8. An assembly as recited in claim 7 wherein said battery charger is integrally connected to said container and is sealed to withstand exposure to the environment present during said sterilization process.

9. An assembly as recited in claim 7 wherein said container includes a connector for releasably electrically connecting said battery housed within said container to said battery charger, said battery charger being distinct from said container and being adapted to releasably engage said connector on the exterior of said container.

10. An assembly as recited in claim 7 wherein said container is further adapted to house a tool during said sterilization process to maintain said tool in a sterile state for use in said sterile field.

* * * * *